(12) United States Patent
Xia et al.

(10) Patent No.: US 11,980,390 B2
(45) Date of Patent: May 14, 2024

(54) CIRCUMCISION EQUIPMENT

(71) Applicant: Wuhu ShangRing Technology Co., Ltd, Anhui (CN)

(72) Inventors: Shujie Xia, Shanghai (CN); Huarong Yu, Beijing (CN); Jingjing Shang, Anhui (CN); Jianzhong Shang, Anhui (CN)

(73) Assignee: Wuhu ShangRing Technology Co., Ltd, Wuhu (CN)

( * ) Notice: Subject to any disclaimer, the term of this patent is extended or adjusted under 35 U.S.C. 154(b) by 1248 days.

(21) Appl. No.: 16/531,139

(22) Filed: Aug. 5, 2019

(65) Prior Publication Data

US 2019/0357931 A1    Nov. 28, 2019

Related U.S. Application Data

(63) Continuation of application No. PCT/CN2018/074988, filed on Feb. 1, 2018.

(30) Foreign Application Priority Data

| Feb. 4, 2017 | (CN) | 201710063339.X |
| Feb. 4, 2017 | (CN) | 201710063340.2 |
| Feb. 4, 2017 | (CN) | 201710065136.4 |
| Feb. 4, 2017 | (CN) | 201710065137.9 |
| Feb. 4, 2017 | (CN) | 201710065138.3 |
| Feb. 4, 2017 | (CN) | 201710065139.8 |
| Feb. 4, 2017 | (CN) | 201710065140.0 |
| Feb. 4, 2017 | (CN) | 201710065146.8 |
| Feb. 4, 2017 | (CN) | 201710065147.2 |
| Feb. 4, 2017 | (CN) | 201710065148.7 |
| Feb. 4, 2017 | (CN) | 201710065149.1 |
| Feb. 4, 2017 | (CN) | 201710065150.4 |
| Feb. 4, 2017 | (CN) | 2017201090340.3 |
| Apr. 18, 2017 | (CN) | 201710250780.9 |
| Apr. 18, 2017 | (CN) | 201710250951.8 |
| Apr. 19, 2017 | (CN) | 201710254989.2 |
| Apr. 19, 2017 | (CN) | 201710255021.1 |
| Apr. 19, 2017 | (CN) | 201710255023.0 |
| Apr. 19, 2017 | (CN) | 201710255025.X |
| Apr. 24, 2017 | (CN) | 201710244426.X |
| Apr. 24, 2017 | (CN) | 201710273894.5 |
| Apr. 24, 2017 | (CN) | 201710273895.X |
| Apr. 24, 2017 | (CN) | 201710274306.X |

(Continued)

(51) Int. Cl.
| *A61B 17/326* | (2006.01) |
| *A61B 17/068* | (2006.01) |
| *A61B 17/115* | (2006.01) |

(52) U.S. Cl.
CPC ........ *A61B 17/326* (2013.01); *A61B 17/0682* (2013.01); *A61B 17/1155* (2013.01)

(58) Field of Classification Search
CPC .............. A61B 17/326; A61B 17/0682; A61B 17/1155
See application file for complete search history.

(56) References Cited

FOREIGN PATENT DOCUMENTS

| CN | 103892890 | * | 7/2014 |
| CN | 204890072 | * | 12/2015 |
| CN | 105962982 | * | 9/2016 |

* cited by examiner

*Primary Examiner* — Thomas McEvoy

(57) ABSTRACT

The present invention relates to surgical devices, particularly to a circumcision equipment, enable the circumcision equipment to be suitable for different surgery objects and environments.

7 Claims, 8 Drawing Sheets

(30) Foreign Application Priority Data

| | | |
|---|---|---|
| Apr. 24, 2017 | (CN) | 201710274307.4 |
| Apr. 24, 2017 | (CN) | 201710274308.9 |
| Apr. 24, 2017 | (CN) | 201710274309.3 |
| Apr. 24, 2017 | (CN) | 201710274396.2 |
| Apr. 24, 2017 | (CN) | 201710274397.7 |
| Apr. 24, 2017 | (CN) | 201710274398.1 |
| Apr. 24, 2017 | (CN) | 201710274399.6 |
| Apr. 24, 2017 | (CN) | 201710274400.5 |
| Aug. 18, 2017 | (CN) | 201710709597.0 |

CIRCUMCISION EQUIPMENT

CROSS REFERENCE TO RELATED APPLICATIONS

The present application is a Continuation Application of PCT Application No. PCT/CN2018/074988 filed on Feb. 1, 2018, which claims the benefit of Chinese Patent Application Nos. 201710063339.X, 201710065146.8, 201710065140.0, 201710065139.8, 201710065138.3, 201710065150.4, 201710065149.1, 201710065148.7, 201710065147.2, 201710063340.2, 201710065137.9, 201710065136.4, 201720109034.3 filed on Feb. 4, 2017, Chinese Patent Application Nos. 201710250780.9 and 201710250951.8 filed on Apr. 18, 2017, Chinese Patent Application Nos. 201710254989.2, 201710255021.1, 201710255023.0 and 201710255025.X filed on Apr. 19, 2017, Chinese Patent Application Nos. 201710274426.X, 201710274400.5, 201710274399.6, 201710274398.1, 201710274397.7, 201710274396.2, 201710274309.3, 201710274308.9, 201710274307.4, 201710274306.X, 201710273895.X and 201710273894.5 filed on Apr. 24, 2017, and Chinese Patent Application No. 201710709597.0 filed on Aug. 18, 2017. All the above are hereby incorporated by reference.

FIELD OF THE INVENTION

The present invention relates to surgical devices, particularly to a built-in washer circumcision device and a valgus washer circumcision device

BACKGROUND OF THE INVENTION

Refer to the built-in washer circumcision device and a valgus washer circumcision device. The redundant prepuce or phimosis is one of the causes of male urinary system infections and sexually transmitted diseases. The redundant prepuce or phimosis can cause urinary tract infections, resulting in chronic prostatitis, with a series of symptoms, such as pains in back and waist, impotence and premature ejaculation. Therefore, the removal of the redundant prepuce is a good way to prevent these diseases.

Traditionally, surgical removal of the phimosis or redundant prepuce has the main technical points of removal of excess prepuce, hemostasis, and apposition suture of cut edges to skin. A postoperative patient cannot move around, suffers unbearable pain in each change of ointment and endures huge pain when stitches are taken out finally. In addition, incomplete ligating hemostasis will cause prepuce hematoma, thus requiring a surgical treatment again. Furthermore, since the prepuce removal and the hemostasis process are performed separately, the operation time is prolonged, and the patient's panic is exacerbated.

A therapeutic method of applying a laser and high-frequency electric surgical knife technology to circumcision has been developed at present. Although this therapeutic method substitutes for scissors cutting and makes a bleeding spot coagulated, the patient's tissues will be burnt and susceptible to infection.

Then, a circumcision device in which a prepuce incision is sutured using suturing nails at one time was developed in this field. However, the suturing nail/U-nail used in the circumcision device in the prior art is generally made of metal. After being tapped into the prepuce of a patient during a surgical operation, the metal U-nail will be in direct contact with the skin, which is likely to cause skin/tissue allergy, even infection, of the patient. In addition, if the U-nail is in direct contact with the skin and tissue of the patient, the possibility that the U-nail inserts into the tissue too deep during the surgery is very high, resulting in damages. Moreover, the U-nail may drop off in a postoperative period as friction between the metal U-nail and the skin/tissue is smaller, which may cause the failure of the surgery due to dropping off of the nail.

SUMMARY OF THE INVENTION

Refer to the built-in washer circumcision device and a valgus washer circumcision device. For the above problems in the prior art, an object of the present invention is to provide a washer circumcision device, and particularly relates to a built-in washer circumcision device and a valgus washer circumcision device. By arranging one or more washers, a U-nail will not be in direct contact with the skin or tissue after being tapped out and fixed to prepuce in a chamfered manner, so that allergy, infection, and too deep tapping of the nail into the tissue or dropping off of the nail are avoided. The specific technical solutions are as follows.

A built-in washer circumcision device comprises a circumcision cover, a comprehensive cover and a first washer and/or a second washer, wherein the comprehensive cover is provided with a U-nail groove; the first washer is arranged in the U-nail groove along the longitudinal outer side of the comprehensive cover; a U-nail seat corresponding to the U-nail groove is arranged on the circumcision cover; and the second washer is arranged on the U-nail seat.

Further, a first ring-shaped groove is formed at the end of the comprehensive cover towards the circumcision cover, and is located outside the U-nail groove; and the first washer is arranged in the first ring-shaped groove.

Further, the first washer is slightly wider than the first ring-shaped groove, so that the first washer is elastically clamped in the first ring-shaped groove.

Further, the first washer has a ring and a protrusion located on the bottom surface of the ring; a second ring-shaped groove is also formed at the end of the comprehensive cover towards the circumcision cover, and is located in the periphery of the first ring-shaped groove; and the protrusion is configured to be clamped in the second ring-shaped groove.

Further, a third ring-shaped groove is formed in the U-nail seat towards the U-nail groove; and the second washer is arranged in the third ring-shaped groove.

Further, the comprehensive cover is provided with a circumcision knife; and a third washer is arranged at the end of the circumcision cover towards the comprehensive cover and corresponds to an anvil of the circumcision knife.

Further, the third washer has a first lateral portion surrounding the anvil, a longitudinal portion perpendicular to the first lateral portion, and a second lateral portion surrounding the U-nail seat.

Further, the first, second and/or third washers are rubber washer(s) and/or silicone washer(s). Further, the built-in circumcision device may be a flat-head-type or inclined-head-type built-in circumcision device.

Further, the first washer is a U-nail backing ring; a protruding positioning ring is arranged on one surface of the U-nail backing ring; a placing groove is formed on the comprehensive cover in the periphery of the first ring-shaped groove; and the positioning ring and the placing groove may be clamped or elastically cooperate with each other to fix the U-nail backing ring.

Both the first and second washers are located on the same axis as a U-nail.

The present invention further provides a valgus washer circumcision device, comprising: an inner comprehensive cover, an inner ring and a first washer and/or a second washer, wherein the inner comprehensive cover and the inner ring correspond to each other vertically; the first washer is arranged at the end of the inner ring towards the inner comprehensive cover; and/or a U-nail groove is formed at the outer edge of the inner comprehensive cover; and the second washer is arranged at the top of the U-nail groove.

Further, both the first and second washers are located on the same axis as a U-nail in the U-nail groove.

Further, a first ring-shaped groove is formed on the lower end surface of the inner ring towards the inner comprehensive cover; and the first washer is arranged in the first ring-shaped groove.

Further, the first washer is slightly wider than the first ring-shaped groove, so that the first washer is elastically clamped in the first ring-shaped groove.

Further, the second washer is arranged outside the U-nail groove, and is located above the opening of the groove.

Further, the second washer has a ring and a protrusion located on the bottom surface of the ring; and the protrusion is configured to be clamped in the U-nail groove.

Further, the second washer is arranged at the top inside the U-nail groove.

Further, the second washer is slightly wider than the U-nail groove, so that the second washer is elastically clamped in the U-nail groove.

Further, a second ring-shaped groove whose top is flush with that of the inner comprehensive cover is formed between the inner edge of the inner comprehensive cover and the U-nail groove; and the second washer is arranged in the second ring-shaped groove.

Further, the valgus washer circumcision device also comprises an upper cover and a lower cover which correspond to each other vertically; the inner comprehensive cover is arranged in the lower cover; the inner ring is arranged in the upper cover; and the inner comprehensive cover and the inner ring correspond to each other vertically.

Compared with the prior art, the present invention provides one or more washer structures. During a circumcision operation, after being tapped out from a U-nail chamber, the U-nail first passes through the washer, so that the main surface of the U-nail will not contact the prepuce skin or tissue after being nailed with the prepuce tissue.

Further, if a plurality of washers is arranged, after being tapped out from a U-nail chamber, the U-nail first passes through the first washer and prepuce tissue sequentially and then the second washer before being in contact with the U-nail seat, and then is clamped in the U-nail seat in a chamfered manner, such that a sandwiched structure comprising the washer, the prepuce and the other washer is formed in the clamped U-nail. Therefore, the possibility that the prepuce tissue is in contact with the metal U-nail is reduced to the greatest extent, so that allergy, infection, too deep tapping of the U-nail into the tissue or dropping off of the U-nail are avoided.

BRIEF DESCRIPTION OF THE DRAWINGS

Refer to the built-in washer circumcision device and a valgus washer circumcision device.

SPECIFIC DESCRIPTION OF THE EMBODIMENTS

Refer to the built-in washer circumcision device and a valgus washer circumcision device. The present invention will be described in detail below with reference to the accompanying drawings. FIGS. 1-9 show preferred embodiments in various embodiments of the present invention.

Figure 1:
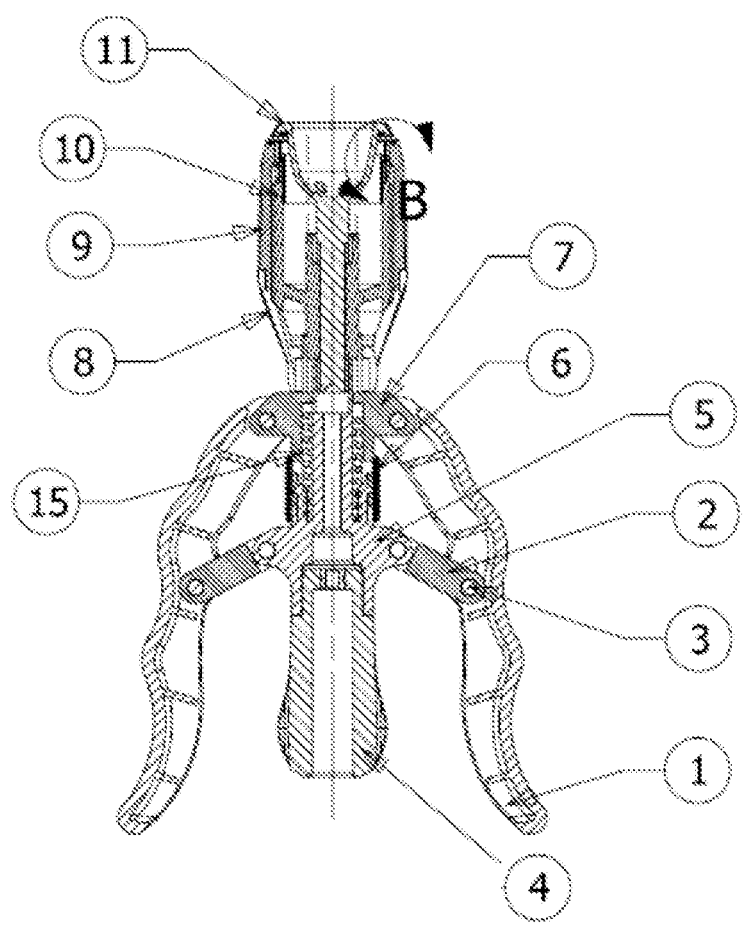
FIG. 1 is an overall view of a circumcision device provided by the present invention.
Figure 2:
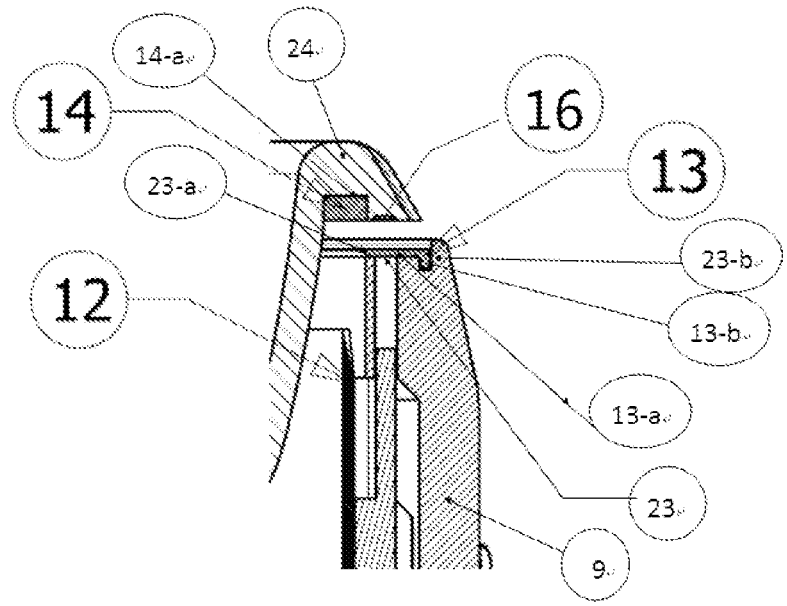
FIG. 2 is a schematically enlarged view of the portion B shown in FIG. 1.
Figure 3:
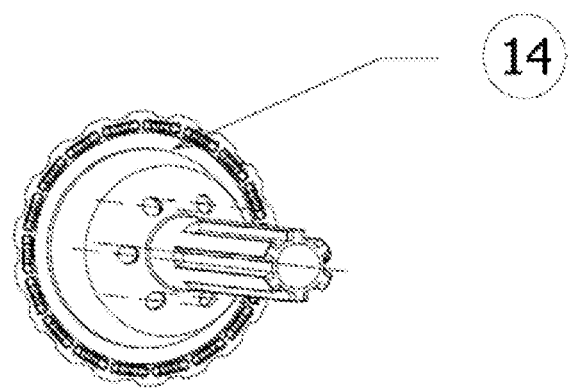
FIG. 3 is a schematically enlarged view of a circumcision cover.

FIGS. 1 and 2 show an overall view of a circumcision device provided by the present invention and a schematically enlarged view of the portion B shown in FIG. 1, respectively. In the figures, 1 represents a handle, 2 a connecting rod, 3 a rivet, 4 a knob, 5 a sheathed core, 6 an opening knob, 7 a sheathed handle, 8 a lower sheath, 9 a comprehensive cover, 10 a thimble, 11 a circumcision cover, 12 a circumcision knife, 13 a first washer 13, 14 a third washer, 15 a spring, and 16 a second washer. The related driving parts, actuating parts, circumcision parts and the like are of common structures in the art. Referring to the drawings, the position relations and connecting relations are both clear; so the details will not be repeated here. The built-in washer circumcision device comprises a circumcision cover 11, a comprehensive cover 9, a first washer 13, and a second washer 16, wherein the comprehensive cover 9 is provided with a U-nail groove 23; the first washer 13 is arranged in the U-nail groove 23 along the longitudinal outer side of the comprehensive cover 9; a U-nail seat 24 corresponding to the U-nail groove 23 is arranged on the circumcision cover 11; and the second washer 16 is arranged on the U-nail seat 24. A first ring-shaped groove 23-*a* is formed at the end of the comprehensive cover 9 towards the circumcision cover 11, and is located outside the U-nail groove 23. The first washer 13 is arranged in the first ring-shaped groove 23-*a*. The first washer 13 has a ring 13-*a* and a protrusion 13-*b* located on the bottom surface of the ring 13-*a*. A second ring-shaped groove 23-*b* is also formed at the end of the comprehensive cover 9 towards the circumcision cover 11, and is located in the periphery of the first ring-shaped groove 23-*a*. The protrusion 13-*b* is configured to be clamped in the second ring-shaped groove 23-*b*. A third ring-shaped groove is formed in the U-nail seat 24 towards the U-nail groove 23. The comprehensive cover 9 is provided with a circumcision knife 12. The third washer 14 is arranged at the end of the circumcision cover 11 towards the comprehensive cover 9 and corresponds to an anvil of the circumcision knife 12. FIG. 3 is a schematically enlarged view of the circumcision cover 11 from another perspective, and shows an individual arrangement of the third washer 14.

Figure 4:
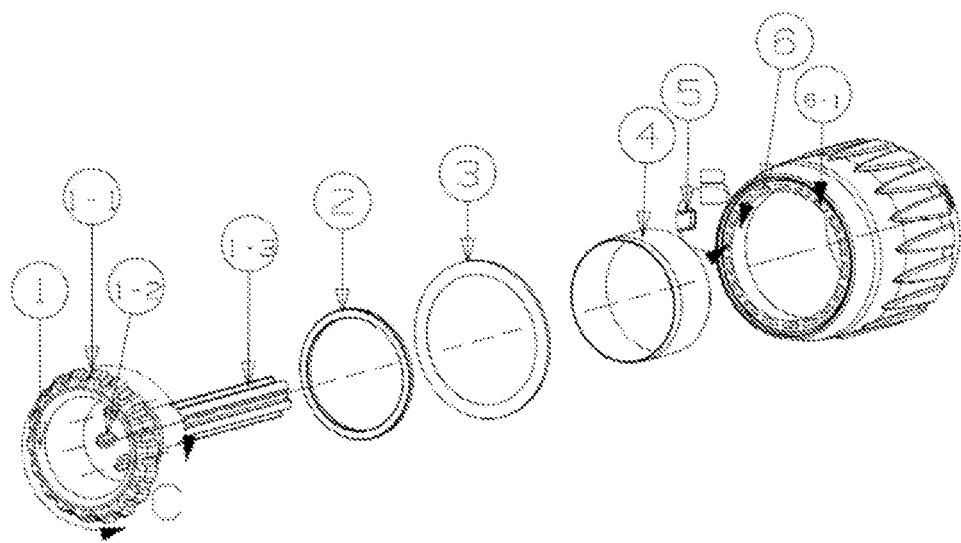
FIG. 4 is a schematically structural view of a flat-head-type built-in circumcision device adopting a washer structure.
Figure 5:
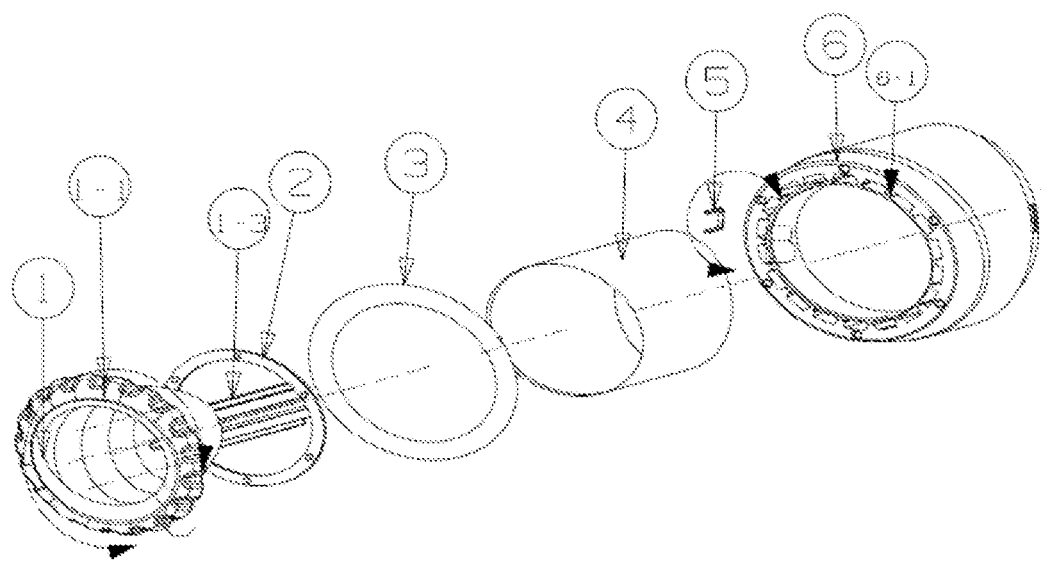
FIG. 5 is a schematically structural view of an inclined-head-type built-in circumcision device adopting a washer structure.
Figure 6:
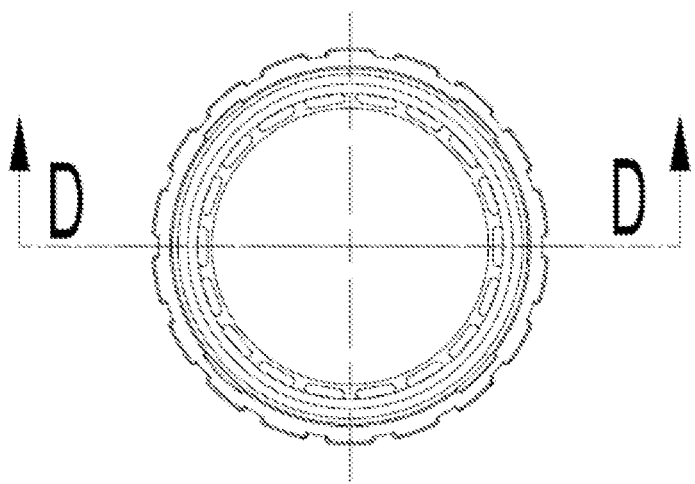
FIG. 6 is a schematic view of a cross section of the comprehensive cover.
Figure 7:
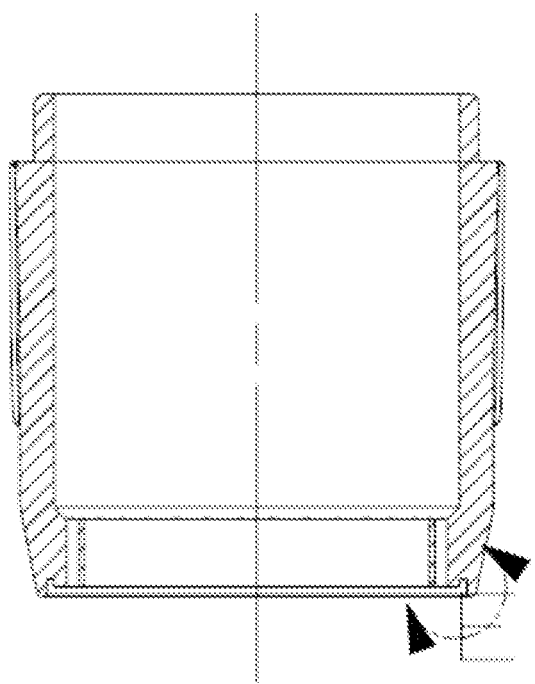
FIG. 7 is a view of D-D shown in FIG. 6.
Figure 8:
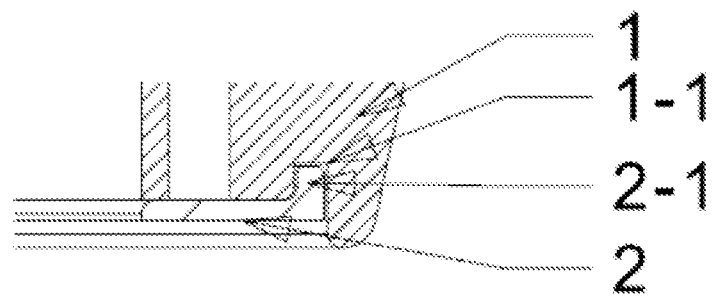
FIG. 8 is an enlarged view of the portion E shown in FIG. 7.
Figure 9:
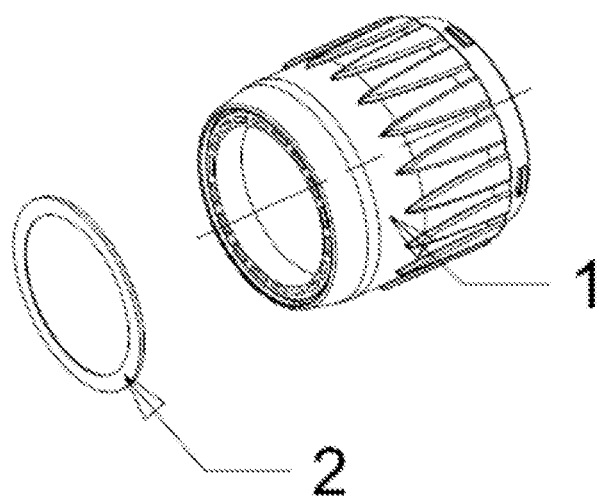
FIG. 9 is a structural relation view between a U-nail backing ring and the comprehensive cover.

FIGS. 4 and 5 show structural views of a flat-head-type built-in circumcision device and an inclined-head-type built-in circumcision device, respectively. In the figures, 1 represents a circumcision cover, 1-1 a blood vessel corresponding groove, 1-2 a negative pressure hole, 1-3 a positioning rod, 1-3-1 a positioning groove, 1-4 a U-nail seat, 2 a circumcision knife washer/a third washer, 3 a U-nail backing ring/a first washer, 4 a circumcision knife, 5 a U-nail, 6 a comprehensive cover, and 6-1 a U-nail groove. The related driving parts, actuating parts, circumcision parts and the like are of common structures in the art. Referring to the drawings, the position relations and connecting relations are both clear; and the details will not be repeated here.

Referring to FIGS. 6-9, in these figures, 1 represents a comprehensive cover, 1-1 a placing groove, 2 a U-nail backing ring and 2-1 a positioning ring. The first washer is the U-nail backing ring 2. The protruding positioning ring 2-1 is arranged on one surface of the U-nail backing ring 2. The placing groove 1-1 is formed on the comprehensive cover 1 in the periphery of the first ring-shaped groove. The positioning ring 2-1 and the placing groove 1-1 may be clamped or elastically cooperate with each other to fix the U-nail backing ring 2.

Figure 10:
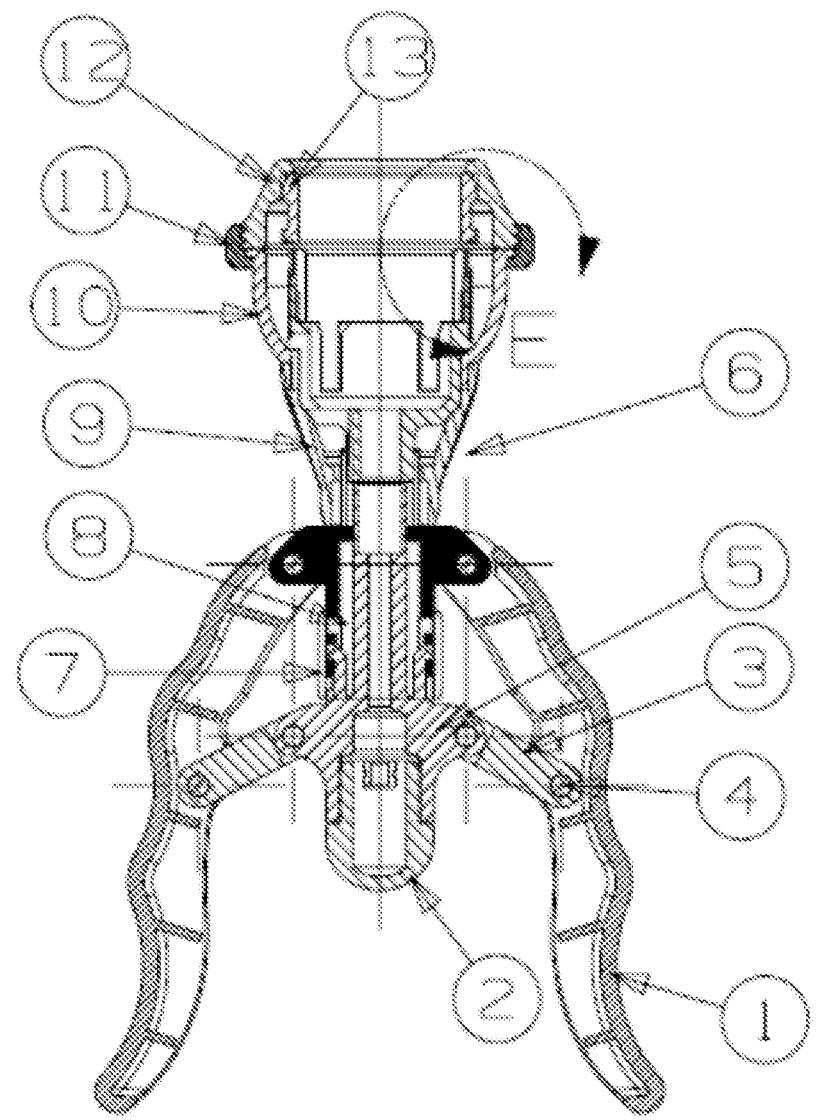
FIG. 10 is another overall view of the circumcision device provided by the present invention.
Figure 11:
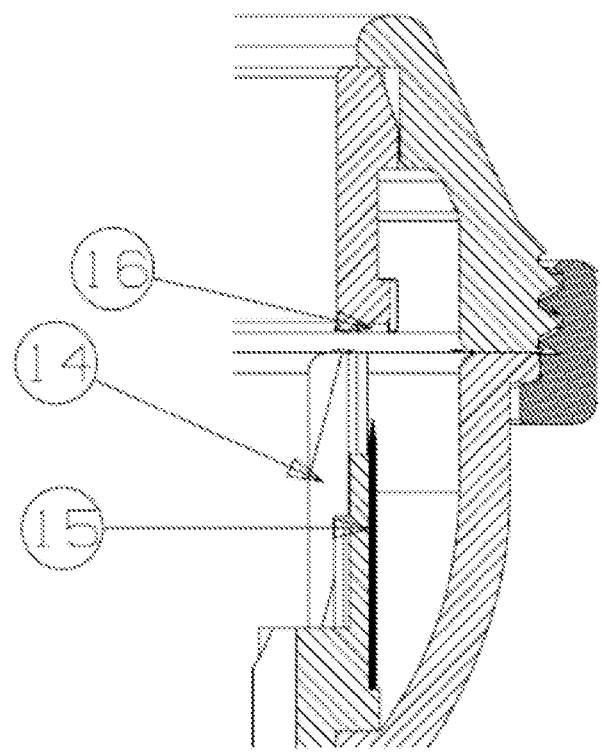
FIG. 11 is a schematically enlarged view of the portion E shown in FIG. 10 in a first solution.

FIGS. 10-13 show preferred embodiments in various embodiments of the present invention. FIGS. 10 and 11 show an overall view of the circumcision device according to the embodiment and a schematically enlarged view of the portion E shown in FIG. 10III in a first solution, respectively. In the figures, 1 represents a handle, 2 a plug, 3 a small connecting rod, 4 a pin, 5 a sliding rod, 6 a connecting block, 7 an opening knob, 8 a spring, 9 a comprehensive cover, 10 a lower cover, 11 a locking ring, 12 an upper cover, 13 an inner ring, 14 an inner comprehensive cover, 15 a ring-shaped blade, and 16 a first washer/U-nail backing ring. The related driving parts, actuating parts, circumcision parts and the like are of common structures in the art. Referring to the drawings, the position relations and connecting relations are both clear; and the details will not be repeated here. Referring to the partial enlarged view shown in FIG. 2, the valgus washer circumcision device comprises an inner comprehensive cover 14, an inner ring 13 and a first washer 16. The inner comprehensive cover 14 and the inner ring 13 correspond to each other vertically. The first washer 16 is arranged at one end of the inner ring 13 towards the inner comprehensive cover 14. The U-nail groove 23 is formed at the outer edge of the inner comprehensive cover 14.

Figure 12:
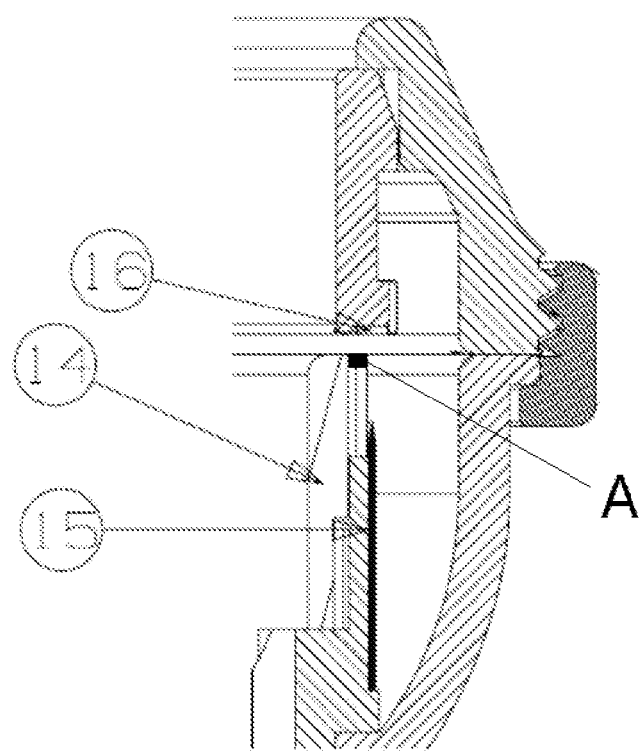
FIG. 12 is a schematically enlarged view of the portion E shown in FIG. 10 in a second solution.

FIGS. 10 and 12 show an overall view of the circumcision device according to the embodiment and a schematically enlarged view of the portion E shown in FIG. 10III in a second solution, respectively. In the figures, 1 represents a handle, 2 a plug, 3 a small connecting rod, 4 a pin, 5 a sliding rod, 6 a connecting block, 7 an opening knob, 8 a spring, 9 a comprehensive cover, 10 a lower cover, 11 a locking ring, 12 an upper cover, 13 an inner ring, 14 an inner comprehensive cover, 15 a ring-shaped blade, 16 a first washer/U-nail backing ring, and a second washer. The related driving parts, actuating parts, circumcision parts and the like are of common structures in the art. Referring to the drawings, the position relations and connecting relations are both clear; and the details will not be repeated here. Referring to the partial enlarged view shown in FIG. 3, the valgus washer circumcision device comprises an inner comprehensive cover 14, an inner ring 13, a first washer 16 and a second washer A. The inner comprehensive cover 14 and the inner ring 13 correspond to each other vertically. The first washer 16 is arranged at one end of the inner ring 13 towards the inner comprehensive cover 14. The U-nail groove is formed at the outer edge of the inner comprehensive cover 14. The second washer is arranged at the top of the U-nail groove. Particularly, the second ring-shaped groove whose top is flush with that of the inner comprehensive cover 14 is formed between the inner edge of the inner comprehensive cover 14 and the U-nail groove; and the second washer A is arranged in the second ring-shaped groove.

Figure 13:
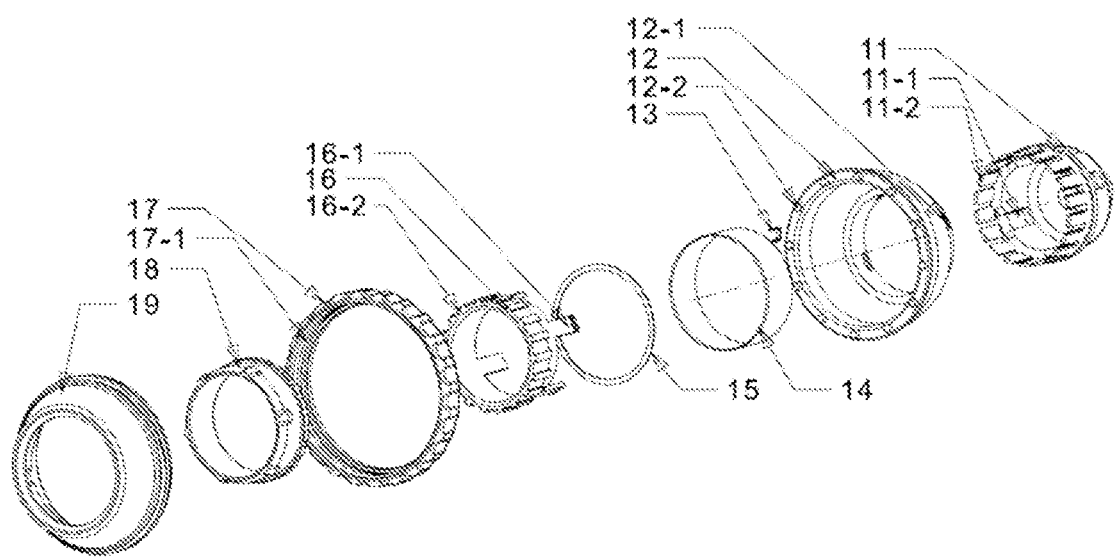
FIG. 13 is an exploded view of a valgus circumcision device; Refer to the blood vessel docking apparatus of a built-in or valgus circumcision device.

FIG. 13 is an exploded view of a valgus circumcision stapler. In the figure, 11 represents a U-nail top ring, 11-1 a groove, 11-2 a U-nail top column, 12 a lower cover, 12-1 a clamping stage, 12-2 a positioning stage, 13 a U-nail, 14 a circumcision knife, 15 a U-nail backing ring/first washer/U-nail backing ring, 16 an inner comprehensive cover, 16-1 a hook, 16-2 a U-nail groove, 17 a locking ring, 17-1 a thread, 18 an inner ring, 18-1 a positioning stage, 18-2 a blood vessel docking groove, 18-3 a U-nail ring washer groove, and 19 an upper cover. The related driving parts, actuating parts, circumcision parts and the like are of common structures in the art. Referring to the drawings, the position relations and connecting relations are both clear; and the details will not be repeated here.

Exemplary descriptions are given for the present invention with reference to the drawings in the above. Obviously, the present invention is not limited to the above implementation manners. Any improvement using the methods, concepts and technical solutions of the present invention or direct application of the present invention to other occasions without modifications shall fall into the protection scope of the present invention.

The above description of the present invention has been given by way of example with reference to the accompanying drawings. It is obvious that the specific implementation of the present invention is not limited to the above modes, and various improvements made using the method concepts and technical solutions of the present invention or directly applied to other occasions, are within the scope of the present invention.

What is claimed is:

1. A built-in washer circumcision device, comprising: a circumcision cover, a comprehensive cover, a first washer, a second washer, the circumcision cover, and the comprehensive cover being configured to be connected with each other, wherein the comprehensive cover is provided with a U-nail groove, and the first washer is arranged in the U-nail groove along a longitudinal outer side of the comprehensive cover at an end of the comprehensive cover facing towards the circumcision cover, wherein the first washer (13) has a ring (13-a) and a protrusion (13-b) located on the bottom surface of the ring; a second ring-shaped groove (23-b) is also formed at the end of the comprehensive cover towards the circumcision cover, and is located in the periphery of the first ring-shaped groove (23-a); and the protrusion (13-b) is configured to be clamped in the second ring-shaped groove (23-b); and a U-nail seat corresponding to the U-nail groove is arranged on the circumcision cover, and the second washer is arranged on the U-nail seat, wherein the comprehensive cover (9) is provided with a circumcision knife (12); and a third washer (14) is arranged at the end of the circumcision cover (9) towards the comprehensive cover and corresponds to an anvil of the circumcision knife (12).

2. The built-in washer circumcision device of claim 1, wherein a first ring-shaped groove is formed at the end of the comprehensive cover towards the circumcision cover, and is located outside the U-nail groove; and the first washer is arranged in the first ring-shaped groove.

3. The built-in washer circumcision device of claim 2, wherein the first washer is slightly wider than the first ring-shaped groove, so that the first washer is elastically clamped in the first ring-shaped groove.

4. The built-in washer circumcision device of claim 1, wherein a third ring-shaped groove is formed in the U-nail seat towards the U-nail groove; and the second washer is arranged in the third ring-shaped groove.

5. The built-in washer circumcision device of claim 1, wherein the first washer, the second washer, and the third washer are rubber washer(s) or silicone washer(s).

6. The built-in washer circumcision device of claim 1, wherein the circumcision device is a flat-head-type or inclined-head-type circumcision device.

7. The built-in washer circumcision device of claim 2, wherein the first washer is a U-nail backing ring; a protruding positioning ring is arranged on one surface of the U-nail backing ring; a placing groove is formed on the comprehensive cover in the periphery of the first ring-shaped groove; and the positioning ring and the placing groove are clamped or elastically cooperate with each other to fix the U-nail backing ring.

\* \* \* \* \*